United States Patent
Diaz et al.

(10) Patent No.: US 7,622,029 B2
(45) Date of Patent: Nov. 24, 2009

(54) ELECTROPOLISHING APPARATUS AND METHOD FOR IMPLANTABLE MEDICAL DEVICES

(75) Inventors: Stephen Hunter Diaz, Palo Alto, CA (US); Jeffrey Bruce Anderson, Santa Rosa, CA (US)

(73) Assignee: Innovational Holdings, LLC., New Brunswick, NJ (US)

( * ) Notice: Subject to any disclaimer, the term of this patent is extended or adjusted under 35 U.S.C. 154(b) by 214 days.

(21) Appl. No.: 11/503,376

(22) Filed: Aug. 11, 2006

(65) Prior Publication Data

US 2007/0034527 A1 Feb. 15, 2007

Related U.S. Application Data

(60) Provisional application No. 60/708,010, filed on Aug. 12, 2005.

(51) Int. Cl.
*C25F 7/00* (2006.01)
*C25F 3/16* (2006.01)

(52) U.S. Cl. .................. 205/686; 205/640; 204/199; 204/212

(58) Field of Classification Search ............. 205/640, 205/686; 204/199, 212
See application file for complete search history.

(56) References Cited

U.S. PATENT DOCUMENTS

| | | | |
|---|---|---|---|
| 2,953,507 A | 9/1960 | Palme | |
| 4,369,101 A * | 1/1983 | Wolff et al. | 204/224 R |
| 4,733,665 A | 3/1988 | Palmaz | |
| 4,739,762 A | 4/1988 | Palmaz | |
| 4,776,337 A | 10/1988 | Palmaz | |
| 6,024,858 A * | 2/2000 | Nishino et al. | 205/139 |
| 6,299,755 B1 | 10/2001 | Richter | |
| 6,375,826 B1 | 4/2002 | Wang et al. | |
| 6,599,415 B1 | 7/2003 | Ku et al. | |
| 6,679,980 B1 | 1/2004 | Andreacchi | |
| 6,726,823 B1 * | 4/2004 | Wang et al. | 205/80 |
| 2005/0098444 A1 | 5/2005 | Schaeffer | |

OTHER PUBLICATIONS

International Search Report dated Jun. 19, 2008 corresponding to International Application No. PCT/US06/31411.

* cited by examiner

*Primary Examiner*—Harry D. Wilkins, III
*Assistant Examiner*—Nicholas A. Smith

(57) ABSTRACT

An electropolishing device for polishing a cylindrical medical device such as a stent includes anodes in the form of rollers arranged to contact an exterior surface of the device. A drive mechanism rotates the anodes periodically during the electropolishing process to change a contact point between the anodes and the medical device. A tilting mechanism can also be used for periodically tilting the anodes during the electropolishing process to allow bubbles to escape from one end of the stent.

19 Claims, 4 Drawing Sheets

ELECTROPOLISHING APPARATUS AND METHOD FOR IMPLANTABLE MEDICAL DEVICES

CROSS REFERENCE TO RELATED APPLICATIONS

This application claims priority to U.S. Provisional Patent Application Ser. No. 60/708,010, filed Aug. 12, 2005, the entire contents of which are incorporated here by reference.

BACKGROUND OF THE INVENTION

1. Field of the Invention

The present invention relates to electropolishing devices and methods, and more particularly to electropolishing devices for polishing stents and other cylindrical medical devices.

2. Summary of the Related Art

In the past, permanent or biodegradable devices have been developed for implantation within a body lumen or blood vessel to maintain patency of the lumen. Once expanded within the blood vessel, these devices, called stents, become encapsulated within the body tissue and provide a permanent or biodegradable support for the vessel wall.

Known stent designs include thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as, stainless steel, gold, silver, tantalum, titanium, cobalt chromium alloys, and shape memory alloys, such as Nitinol.

Stents are often formed by cutting a pattern into a tube, such as a stainless steel or cobalt chromium alloy tubes with a laser. However, laser cutting and other metal forming operations tend to leave burrs and sharp edges which are undesirable on implantable devices. The stents will be in contact with tissue and burrs and sharp edges can cause tissue irritation. Tissue irritation caused by burrs and rough surfaces on stents can be one of the causes of restenosis or the re-occlusion of a blood vessel after balloon angioplasty and stenting. In addition, when sharp edges, burrs, or other marks are on the inside of stents they can cause disturbance in the blood flow through a blood vessel which can cause the blood to clot. Electropolishing is a process used for providing a smooth surface on metal parts including implantable metallic devices, such as stents.

Electropolishing involves immersing a metallic object into an electrolyte solution in the presence of an electric current which causes protrusions on the metal object to be dissolved. The metallic object, such as the stent, is positioned in contact with an anode or positive electrode, while a cathode or negative electrode is positioned in the electrolyte solution nearby. As the electric current passes through the metallic object and electrolyte solution, from the anode to the cathode, metal is removed from the object. However, the metal is removed faster at the locations of protruding portions of the metal due to a concentration of the current at these locations. The dissolving of the protrusions faster than the remaining metal surfaces results in a very smooth and polished surface.

U.S. Pat. Nos. 6,299,755; 6,375,826; 6,599,415; and 6,679,980 disclose systems for electropolishing stents. Although electropolishing is an effective method for obtaining smooth surfaces on stents, electropolishing processes are very sensitive. Repeatable and even polishing is difficult to achieve. The uniformity of the polished surface depends on factors including on the uniformity of the current density across the surfaces. The current density is particularly uneven at the contact points where the anode is in contact with the metal surface. The high current density at the contact point result in particularly aggressive polishing around the contact points. In addition, the metal contact member, which may be a clip, a wire, or a roller, can mask the current and cause a high point. These contact points result in contact marks on the polished products which are undesirable.

Accordingly, an electropolishing fixture which minimized current density differences and substantially eliminates contact marks on the products is needed. In addition, it would be desirable to provide overall even electropolishing.

SUMMARY OF THE INVENTION

In accordance with one aspect of the present invention, an electropolishing device process comprises the steps of placing a substantially cylindrical medical device onto a plurality of anodes in the form of rollers with the rollers contacting an exterior of the medical device, placing the medical device into an electrolytic solution, applying a current between the anodes and a cathode positioned in the electrolytic solution, and periodically turning off the current and rotating the anodes to change contact points between the anodes and the medical device.

In accordance with one aspect of the present invention an electropolishing process comprises the steps of placing a substantially cylindrical medical device onto a plurality of anodes in the form of rollers with the rollers contacting an exterior of the medical device, holding the medical device in place on the anodes with an idle roller, placing the medical device into an electrolytic solution, applying a current between the anodes and a cathode positioned in the electrolytic solution, and periodically rotating the anodes to change contact points between the anodes and the medical device.

In accordance with another aspect of the invention an electropolishing process comprises the steps of placing a substantially cylindrical medical device onto a plurality of anodes, placing the medical device into an electrolytic solution with an axis of the medical device tilted to allow bubbles to escape from a first end of the medical device, applying a current between the anodes and a cathode positioned in the electrolytic solution, and periodically turning off the current and tilting the medical device to change an orientation of the medical device axis to allow bubbles to escape from a second end of the medical device.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
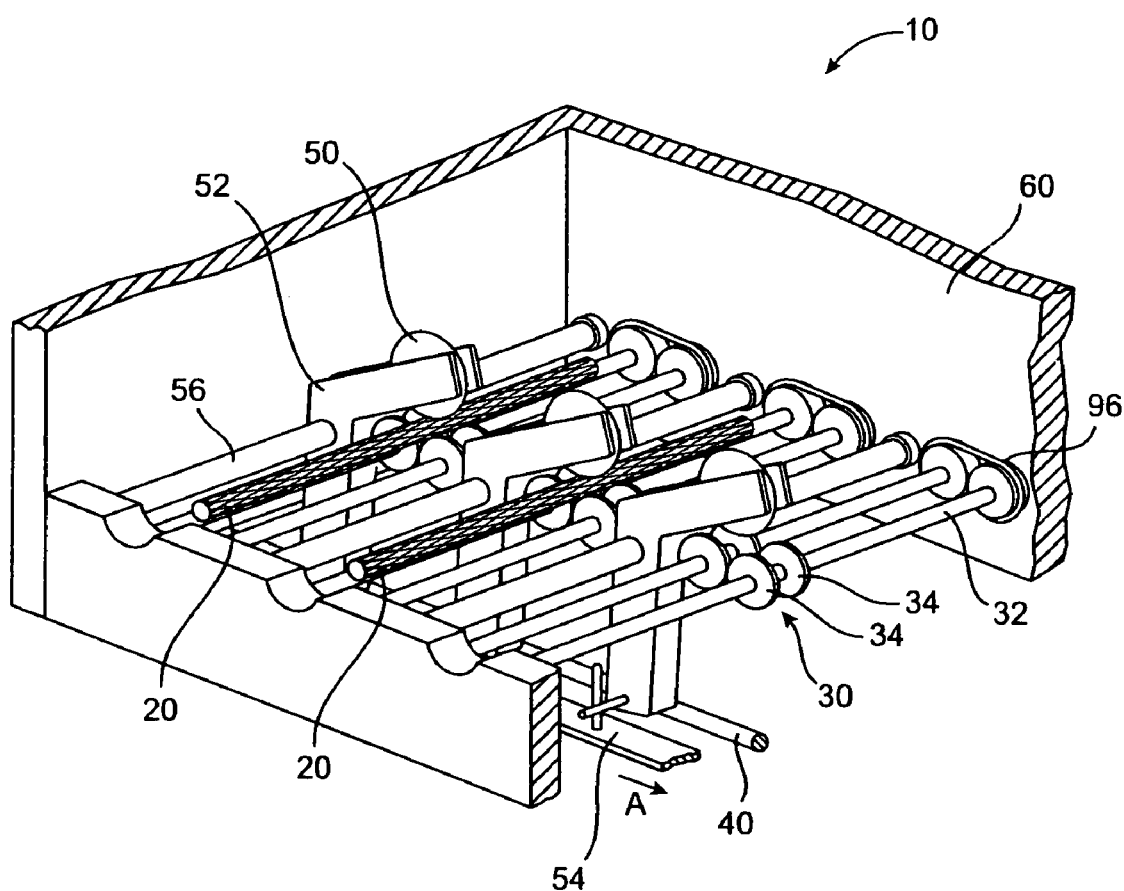
FIG. 1 is a perspective view of a portion of an electropolishing fixture according to the present invention.

FIG. 1 illustrates a portion of a polishing fixture 10 for use in electropolishing implantable medical devices, such as stents. The polishing fixture 10 is used to hold the medical devices when they are immersed in an electrolyte solution in an electropolisher. FIG. 1 illustrates two medical devices or stents 20 positioned in the fixture 10. The stents 20 are laser cut from a metal tube to form expandable, substantially cylindrical devices.

The electropolisher into which the polishing fixture 10 and stents 20 are immersed during electropolishing is not shown. Electropolishers are commercially available and are used to polish and deburr small, precision machined, metallic items. The electropolisher equipment is generally constructed of stainless steel or from other non-corroding alloys. The electrolyte solution is provided in a tank within the electropolisher and the electrolyte solution temperature is automatically controlled by a heater and cooling fan combination of the electropolisher. The electropolisher also provides precision timing and electrical control for the process which are connected to the electropolishing fixture 10 and used to control the functions of the fixture.

Electrolyte solutions are commercially available from electropolisher manufacturers and are available for stainless-steel, cobalt chromium alloys, nickel-chrome alloys, and other metals.

The polishing fixture 10 of FIG. 1 includes a plurality of anodes 30 and a cathode 40 formed of a conductive material. The polishing fixture 10 is configured to rotate and tilt the stents and eliminate the need for stirring the electrolyte solution. Each of the anodes 30 include a rotatable rod 32 and two anode rollers 34. A pair of anodes 30 each having two rollers 34 support each stent 20 and provide electrical and mechanical contact at four points on each stent. A drive mechanism, which will be described below, rotates the anode rollers 34 and thus, rotates the stents periodically throughout the electropolishing process to change the contact points and limit the occurrence of contact marks on the finished stent. The anodes 30 are arranged to contact only exterior surfaces of the stent 20 to eliminate contact marks on the interior of the stent. Contact marks and other irregularities on the interior surfaces of stents can possibly contribute to restenosis and thrombosis. The anode rollers 34 can be smooth or grooved. Although four anode rollers 34 are illustrated supporting each stent, three rollers, or more than four rollers can also be used. However, limited numbers of rollers are desirable to limit the contact marks and to improved the uniformity of flow of liquid around the stent.

In addition to the anodes 30, the stents 20 are retained within the electropolishing fixture by movable idle rollers 50 formed of insulating material. The idle rollers 50 are mounted on idle roller arms 52 which position the idle rollers above the stents 20 to prevent the stents from losing electrical contact with the anodes 30. The idle rollers 50 can be maintained in contact with the stents 20 during polishing by either the weight of the rollers and arms or by spring force of an associated spring mechanism. As shown in FIG. 1, the idle rollers 50 can be moved out of the way for loading and unloading of the stents 20 by sliding a sliding bar opening mechanism 54 in the direction of the arrow A to rotate the idle roller arms 52 and idle roller support rods 56. Although one idle roller 50 per stent 20 is shown, additional idle rollers may also be provided.

The anode rods 32 and rods 56 on which the idle roller arms 52 rotate are rotatably mounted within an insulated support frame 60 of the electropolishing fixture 10. The support frame 60 is designed to hold multiple stents 20, such as 4-20 stents for simultaneous electropolishing. Although each stent 20 is provided with multiple anodes 30 a single cathode 40 is provided which runs perpendicular to the axes of the stents and beneath the stents to provide a consistent current density to the multiple stents. The location and shape of the cathode will affect the uniformity of material removal. The rod cathode rather than a conventional screen or cylindrical cathode has been found to provide more uniform polishing. The best configuration will depend on the size and shape of the objects being polished.

The anode and cathode materials are selected depending on the material of the stents 20 and the electrolyte solution. Electrode materials may include titanium, nickel-titanium alloys, platinum, platinum-iridium alloys, zirconium, and zirconium alloys. The support frame 60, housing 80, and drive elements are made of acid resistant insulating polymer materials, such as ultra high molecular weight polyethylene or Kynar.

The spacing between the anode rollers 34 is customized to accommodate the particular medical device being polished. Many stent designs include a plurality of cylindrical members which provide radial support to a vessel wall and which are interconnected by thinner and more flexible bridging elements (not shown) which provide axial flexibility to the stent. A typical stent includes a repeating pattern of cylindrical elements and bridging elements. Since the bridging elements are thinner than the cylindrical elements of the stent they are less suitable for conducting larger polishing currents to the part. Therefore, the anodes should be spaced so that both anodes will not be positioned on stent bridging elements. Thus, the anode rollers 34 should be positioned on the rods 32 at a spacing which is different from the repeating pattern of the stents.

The spacing between the anode rods 32 in each pair is dependant on the diameters of the stents 20 and the rollers 32. The diameter of the anode rollers 34 is at least 50% of the diameter of the stents 20, and preferably at least equal to the diameter of the stents.

The anode rollers 34 are rotated with each roller in a pair rotating in the same direction by a drive mechanism. The drive mechanism may include any combination of drive elements, such as belts and gears. The rotation of the anode rollers 34 periodically throughout the electropolishing process moves the anode contact point on the stent and minimizes the occurrence of contact marks on the polished stents 30. For a typical about 8 minute electropolishing process, the contact point is adjusted by rotation of the anode rollers sixteen times, or about every 30 seconds. The rotation can be any amount which results in a different contact point at each rotation. For example, the stent can be rotated about 20 degrees, 340 degrees, or 380 degrees at each rotation. This pattern assures maximum evenness of polishing in the radial direction. The polishing current is turned off or disconnected when the two anode rollers 34 are turning to prevent arcing that might mark the surface. Because the rate of polishing is proportional to the electric current, a separate constant current power supply is used for each stent.

Figure 2:
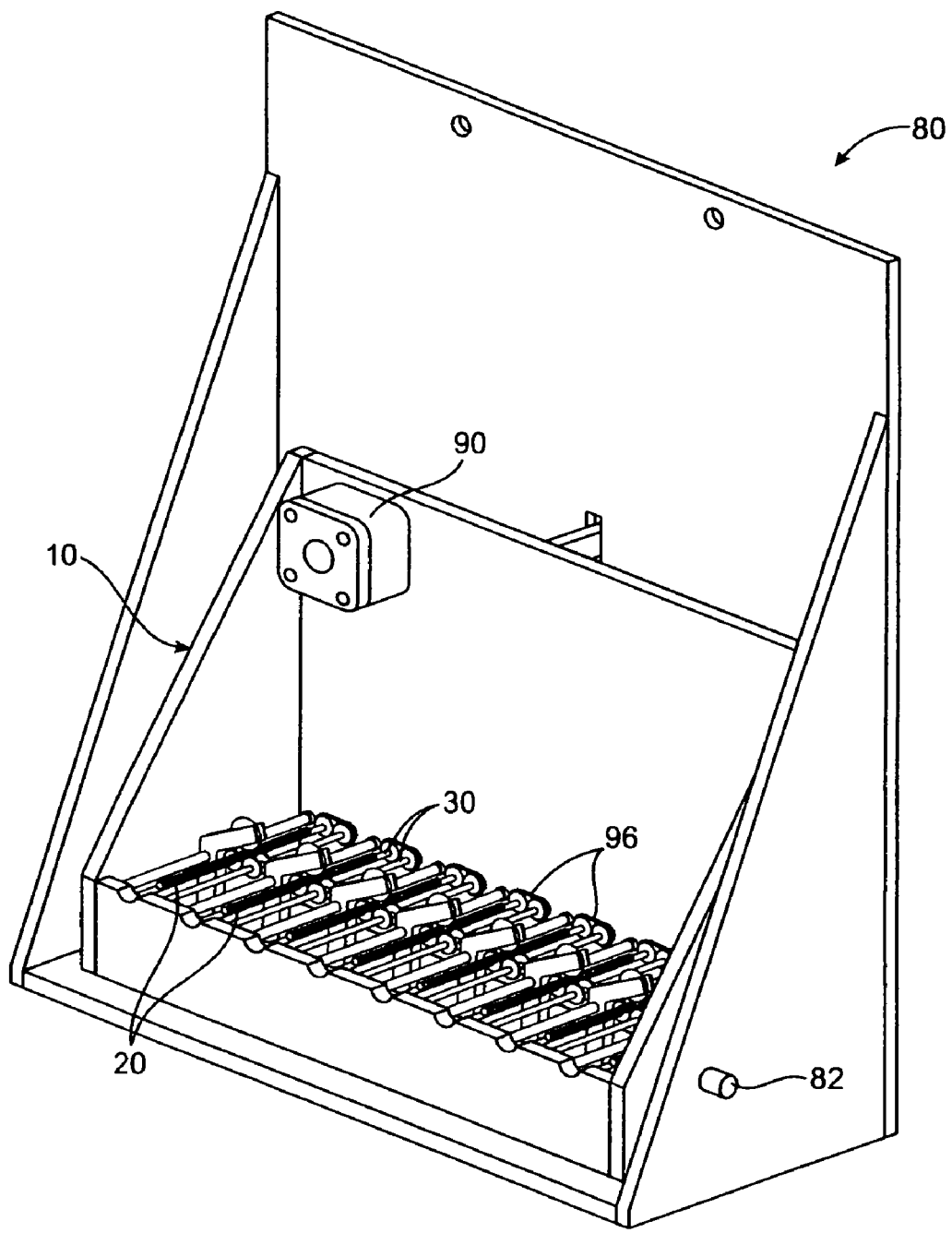
FIG. 2 is a perspective view of the electropolishing fixture of FIG. 1 in a housing.
Figure 3:
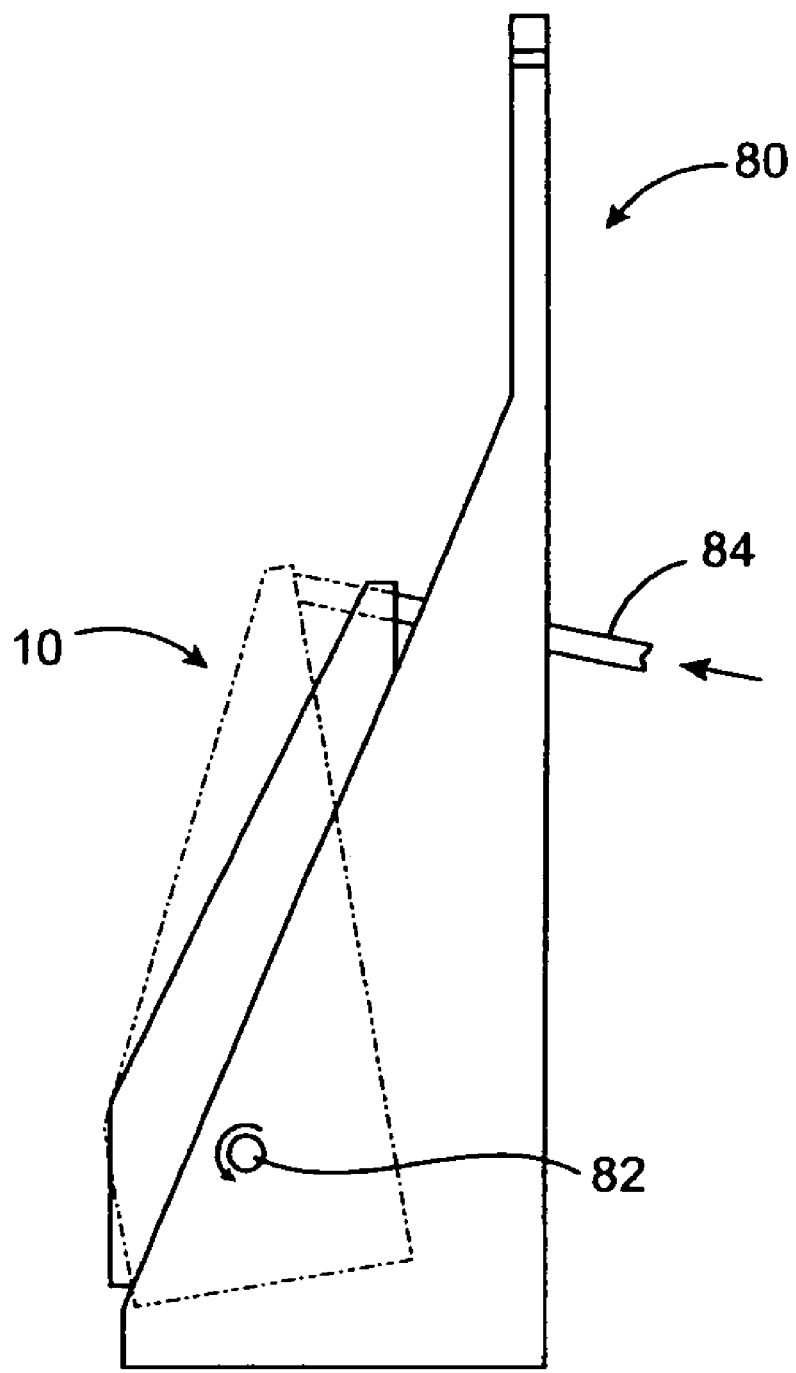
FIG. 3 is a side view of the electropolishing fixture housing of FIG. 2.

FIGS. 2 and 3 illustrate the polishing fixture 10 mounted in an insulating housing 80. The polishing fixture 10 is rotatable in the housing 80 about an axis 82 to allow the stents 20 to be tipped back and forth during electropolishing. Tipping the stents 20 will allow bubbles to escape from either end of the stent. The axis 82 about which the fixture 10 is rotated is substantially perpendicular to an axis of the stents 20 placed on the anodes 30. The tilting of the stents 20 during electropolishing improves the longitudinal uniformity of the electropolishing process by varying the way in which bubbles created during polishing escape from an interior of the stent. These bubbles can escape from an end of the stent more easily when the stent is tilted. However, the bubbles can also increase turbulence at the end of the stent as they escape which can increase the polishing at this area. Therefore, the polishing fixture 10 is preferably tilted at least once during polishing to distribute the high polishing areas caused by the bubbles evenly to both ends of the stent. The fixture 10 can also be tilted repeatedly during polishing. The degree of tilting can vary from about 3 degrees to about 45 degrees, and is preferably in the range of about 5 degrees to about 20 degrees. As shown in FIG. 3, the tilting of the polishing fixture 10 is provided by an actuator rod 84 which is driven by any known drive mechanism. The polishing current is turned off during tilting of the polishing fixture 10 to prevent arcing that might mark the stent.

Figure 4:
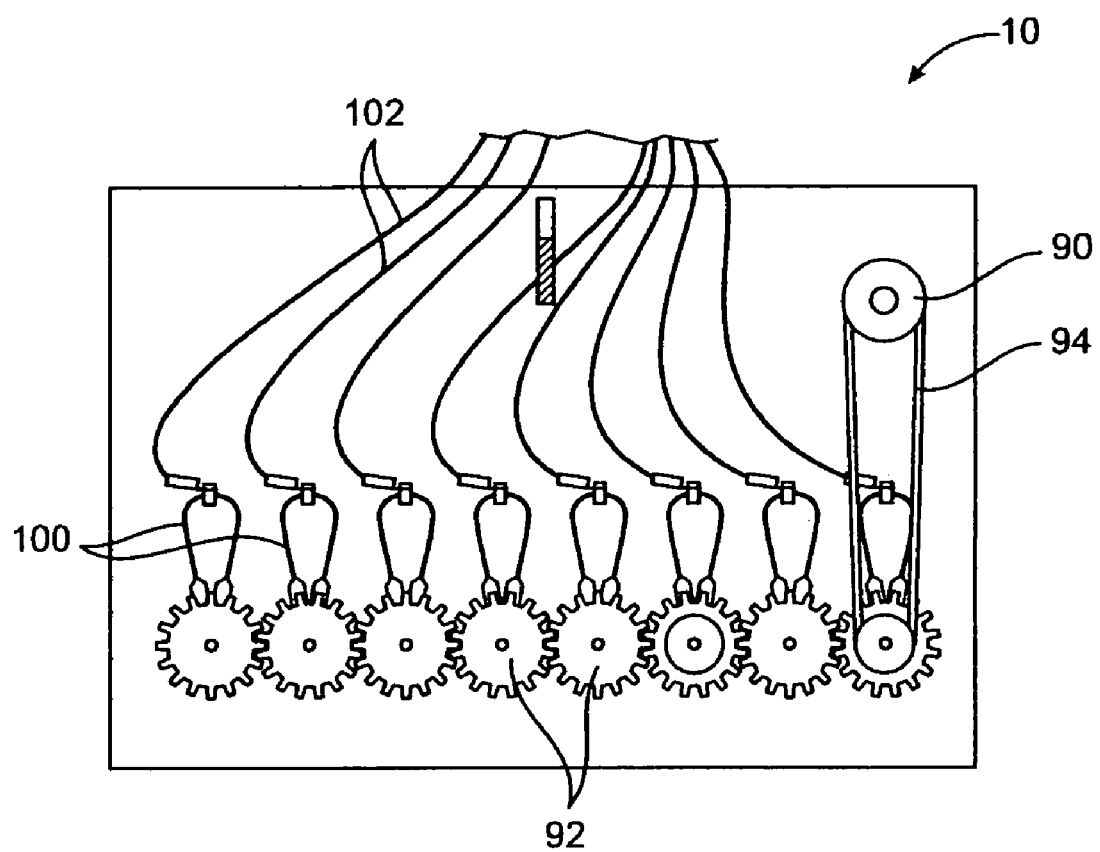
FIG. 4 is a back view of the electropolishing fixture of FIG. 1.

A motor 90, shown in FIG. 2, is provided on the polishing fixture 10 for rotating the rods 32 of the anodes 30. FIG. 4 shows the back side of the polishing fixture 10 and the drive mechanism arrangement for rotating the anodes 30. Although the drive mechanism shown and described herein includes a combination of belts and gears, other drive systems can also be used. The drive mechanism shown includes a plurality of gears 92 connected to one of each pair of anodes and a belt 94 connecting the motor 90 to the gears. Each of the pairs on anodes 30 is interconnected by an anode drive belt 96 on the front side of the polishing fixture 10 as shown in FIGS. 1 and 2. Thus, the rotation of the motor 90 is transmitted by the belt 94, the gears 92, and the anode belts 96 to each of the anode rollers 34 to rotate the stents 20.

FIG. 4 also illustrates one example of a electrical contact system for connection to each of the anodes 30. A spring loaded anode clip 100 connected to an electrical lead 102 is pressed into contact with each pair of anode rods 32 to provide electrical contact with the anodes. The spring loaded clip allows the anode rods 32 to rotate while maintaining electrical contact with the rods. Each of the anode pairs is independently controlled by the electropolisher electrical control system.

While the invention has been described in detail with reference to the preferred embodiments thereof, it will be apparent to one skilled in the art that various changes and modifications can be made and equivalents employed, without departing from the present invention.

The invention claimed is:

1. An electropolishing process comprising:
   placing a substantially cylindrical medical device onto a plurality of anodes in the form of rollers with the rollers contacting an exterior of the medical device;
   holding the medical device in place on the anodes with an idle roller;
   placing the medical device into an electrolytic solution;
   applying a current between the anodes and a cathode positioned in the electrolytic solution; and
   periodically rotating the anodes to change contact points between the anodes and the medical device; and
   wherein each periodic rotation of the plurality of anodes results in rotation of the medical device about one revolution about a longitudinal axis.

2. The electropolishing process of claim 1, wherein the plurality of anodes contact only with the exterior surface of the medical device.

3. The electropolishing process of claim 1, wherein the plurality of anodes are rotated at least 4 times during the electropolishing process.

4. The electropolishing process of claim 1, wherein the plurality of anodes are rotated at least 10 times during the electropolishing process.

5. An electropolishing process comprising:
   placing a substantially cylindrical medical device onto a plurality of anodes in the form of rollers with the rollers contacting an exterior of the medical device;
   holding the medical device in place on the anodes with an idle roller;
   placing the medical device into an electrolytic solution;
   applying a current between the anodes and a cathode positioned in the electrolytic solution; and
   periodically rotating the anodes to change contact points between the anodes and the medical device;
   wherein an axis of the medical device is positioned at an angle during the electropolishing process to allow bubbles to escape from a first end of the medical device.

6. The electropolishing process of claim 5, wherein the medical device is tilted during the electropolishing process to allow bubbles to escape from a second end of the medical device.

7. The electropolishing process of claim 1, wherein the plurality of anodes are formed of titanium.

8. An electropolishing process comprising:
   placing a substantially cylindrical medical device onto a plurality of anodes in the form of rollers with the rollers contacting an exterior of the medical device;
   holding the medical device in place on the anodes with an idle roller;
   placing the medical device into an electrolytic solution;
   applying a current between the anodes and a cathode positioned in the electrolytic solution; and
   periodically rotating the anodes to change contact points between the anodes and the medical device; and
   wherein the cathode is a wire rod positioned below and running substantially perpendicular to the axis of a medical device placed on the anodes.

9. The electropolishing process of claim 1, wherein the cathode is a zirconium wire.

10. The electropolishing process of claim 1, wherein the plurality of anodes provide four contact points on an exterior of the medical device.

11. The electropolishing process of claim 1, wherein the idle roller provides one contact point with the medical device.

12. An electropolishing process comprising:
   placing a substantially cylindrical medical device onto a plurality of anodes in the form of rollers with the rollers contacting an exterior of the medical device;
   placing the medical device into an electrolytic solution;
   applying a current between the anodes and a cathode positioned in the electrolytic solution; and
   periodically turning off the current and rotating the anodes to change contact points between the anodes and the medical device.

13. The electropolishing process of claim 12, wherein the plurality of anodes contact only with the exterior surface of the medical device.

14. The electropolishing process of claim 12, wherein the plurality of anodes are rotated at least 4 times during the electropolishing process.

15. The electropolishing process of claim 12, wherein the plurality of anodes are rotated at least 10 times during the electropolishing process.

16. The electropolishing process of claim 12, wherein each periodic rotation of the plurality of anodes results in rotation of the medical device about one revolution.

17. The electropolishing process of claim 12, wherein an axis of the medical device is positioned at an angle during the electropolishing process to allow bubbles to escape from a first end of the medical device.

18. An electropolishing process comprising:
   placing a substantially cylindrical medical device onto a plurality of anodes;
   placing the medical device into an electrolytic solution with an axis of the medical device tilted to allow bubbles to escape from a first end of the medical device;
   applying a current between the anodes and a cathode positioned in the electrolytic solution; and
   periodically turning off the current and tilting the medical device to change an orientation of the medical device axis to allow bubbles to escape from a second end of the medical device.

19. The electropolishing process of claim 18, wherein the periodic turning off and tilting is performed automatically.

* * * * *